US006523954B1

(12) United States Patent
Kennedy et al.

(10) Patent No.: US 6,523,954 B1
(45) Date of Patent: Feb. 25, 2003

(54) SYSTEM AND METHOD FOR EYE SCREENING

(75) Inventors: Ross A. Kennedy, Burnaby (CA); Jack R. Bellows, Memphis, TN (US); David E. Thomas, Bartlett, TN (US)

(73) Assignee: iScreen, LLC, Memphis, TN (US)

( * ) Notice: Subject to any disclaimer, the term of this patent is extended or adjusted under 35 U.S.C. 154(b) by 0 days.

(21) Appl. No.: 09/718,058

(22) Filed: Nov. 21, 2000

(51) Int. Cl.[7] ................................................ A61B 3/10
(52) U.S. Cl. ...................................................... 351/205
(58) Field of Search ................................ 351/205, 206, 351/221, 237, 239, 246; 600/319, 320, 318; 128/904, 903, 920, 922, 923, 925

(56) References Cited

U.S. PATENT DOCUMENTS

| | | | |
|---|---|---|---|
| 4,569,354 A | 2/1986 | Shapiro et al. | 128/665 |
| 4,586,796 A | 5/1986 | Molteno | 351/206 |
| 4,669,836 A | 6/1987 | Richardson et al. | 351/206 |
| 4,950,069 A | 8/1990 | Hutchinson | 351/210 |
| 5,139,030 A | 8/1992 | Seay, Jr. | 128/745 |
| 5,218,387 A | 6/1993 | Ueno et al. | 351/210 |
| 5,303,709 A | 4/1994 | Dreher et al. | 128/665 |
| 5,355,895 A | 10/1994 | Hay | 128/745 |
| 5,632,282 A | 5/1997 | Hay et al. | 128/745 |
| 5,864,384 A | 1/1999 | McClure et al. | 351/224 |
| 5,898,474 A | 4/1999 | McClure et al. | 351/224 |
| 5,943,116 A * | 8/1999 | Zeimer | 351/221 |
| 5,989,194 A | 11/1999 | Davenport et al. | 600/558 |
| 5,993,001 A | 11/1999 | Bursell et al. | 351/212 |
| 6,003,991 A | 12/1999 | Viirre | 351/206 |
| 6,027,217 A | 2/2000 | McClure et al. | 351/224 |
| 6,033,070 A | 3/2000 | Kearns | 351/168 |
| 6,089,715 A | 7/2000 | Hoover et al. | 351/221 |
| 6,305,804 B1 * | 10/2001 | Rice et al. | 351/221 |

OTHER PUBLICATIONS

Barnes, GT; Morin, RL; Staab, EV, "infoRAD: computers for clinical practice and education in radiology. Teleradiology: fundamental considerations and clinical applications" *RadioGraphics* (1993) 13:673–681.

Batnitzky, S; Rosenthal, SJ; Siegel, EL; Wetzel, LH; Murphy, MD; Cox, GG; McMillan, JH; Templeton, AW and Dwyer, SJ, "Teleradiology: an assessment" *Radiology* (1990) 177:11–17.

Becker, Jo, "Eye exam's necessity is challanged" *St. Petersburg Times* (Jun. 2, 1999) p. 113.

(List continued on next page.)

Primary Examiner—George Manuel
(74) Attorney, Agent, or Firm—Woodard, Emhardt, Naughton, Moriarty & McNett

(57) ABSTRACT

A system and method for eye screening is provided. The system may include a remote data entry device for receiving patient information and eye images. A centralized facility is provided to receive data from the remote device and pass the information to still further remote reading centers. The method provides for eye screening by readers at a site remote from the patient. Furthermore, the method contemplates maintaining the quality of reader output through electronic monitoring and training.

23 Claims, 10 Drawing Sheets

OTHER PUBLICATIONS

Brown, PH; Krishnamurthy, GT, "Design and operation of a nuclear medicine picture archiving and communication system" *Semin Nucl Med* (1990) 20(3):205–224.

Campbell, Melanie C.W.; Bobier, W.R.; Roorda, A., "Effect of monochromatic aberrations on photorefractive patterns" *J. Opt. Soc. Am. A* (1995) 12(8):1637–1646.

Casey, FA, "Telemedicine in paediatric cardiology" *Arch Dis Child* (1999) 80:497–499.

Cox, RD; Henri, CJ; Rubin, RK, "Transparent image access in a distributed picture archiving and communications system: the Master Database broker." *J Digit Imaging* (1999) 12(2):175–177.

de Valk, JP; Ottes, FP; Seeley, GW, "Feasible (I): The PC software package for feature evaluation and system inspection by logged experiments." *Med Inform (Lond)* (1988) 13(4):331–336.

Donahue, Sean P.; Johnson, Tammy M.; Leonard–Martin, Thomas C., "Screening for Amblyogenic Factors Using a Volunteer Lay Network and the MTI PhotoScreener" *Opthalmology* (2000) 107(9):1637–1646.

Dwyer, SJ $3^{rd}$; "Imaging system architectures for picture archiving and communication systems." *Radiol Clin North Am* (1996) 34(3):495–503.

Elion, JL; Petrocelli, RR, "A high–speed network for cardiac image review." *Proc Annu Symp Comput Appl Med Care* (1994) 428–432.

Freedman, Howard L, Preston, Karen L, "Polaroid Photoscreening for Amblyogenic Factors, An Improved Methodology" *Opthalmology* 99(12):1785–1795.

Gekeler, Florian, Schaeffel, Frank; Howland, Howard C.; Wattam–Bell, John, "Measurement of Astigmatism by Automated Infrared Photoretinoscopy" (1997) 74(7):472–482.

Granet, David B.; Hoover, Adam; Smith, Amanda R.; Brown, Stuart I.; Bartsch, Dirk–Uwe; Brody, Barbara, "A New Objective Digital Computerized Vision Screening System" *Journal of Pediatric Opthalmology & Strabismus* (1999) 36(5):251–256.

Hodgkinson, I.J.; Chong, K.M.; Molteno, A.C.B., "Characterization of the Fundal Reflectance of Infants" *Optometry and Vision Science*(1991) 68(7):513–521.

Hodgkinson, Ian J.; Bosma, Nicola J.; Molteno, A.C.B. "Chromatic Analysis of Photorefraction: A Model for the Otago Photoscreener" *Australasian Physican & Engineering Sciences in Medicine* (1994) 17(3):101–107.

Hodgkinson, Ian J.; Chong, K.M.; Molteno, A.C.B. "Photorefraction of the living eye: a model for linear knife edge photoscreening" *Applied Optics* (1991) 30(16):2263–2269.

Howland, Howard C.; Howland, Bradford, "Photorefraction: a technique for study of refractive state at a distance" *Journal of the Optical Society of America* (1974) 64(2):240–249.

Howland, Howard C.; Braddick, Oliver; Atkinson, Janet; Howland, Bradford, "Optics of photorefraction: orthogonal and isotropic methods" *J. Opt. Soc. Am.* 73(12):1701–1708.

Hwang, SC; Lee, MH, "A WEB–based telePACS using an asymmetric satellite system." *IEEE Trans Inf Technol Biomed* (2000) 4(3):212–215.

Johnson, Roger A.; Blair, Rose J.; Zaba, Joel, "The Visual Screening of Title I Reading Students" *Journal of Behavioral Optometry* (2000) 11(1):3–6.

Kemper, Alex R.; Margolis, Peter A.; Downs, Stephen M.; Bordley, W. Clayton, "A Systematic Review of Vision Screening Tests for the Detection of Amblyopia" *Pediatrics* (1999) 104(5):1220–1222.

Kennedy, Ross A.; Sheps, Samuel B., "A comparison of photoscreening techniques for amblyogenic factors in children" *Can J. Opthalmol* (1989) 24(6):259–264.

Kusel, Reinhard; Oechsner, Ulrich; Wesemann, Wolfgang; Russlies, Stephan; Irmer, Eva M. and Rassow, Bernard, "Light–intensity distribution in eccentric photorefraction crescents" *J. Opt. Soc. Am. A* (1998) 15(6):1500–1511.

Lowe, HJ; Antopov, I; Hersh, W.; Smith CA "Towards knowledge–based retrieval of medical images. The role of semantic indexing, image content representation and knowledge–based retrieval." *Proc AMIA Symp* (1998) 882–6.

Maddison, I, "The Internet and radiology" *Br J Radiol* (1997) 70 Spec No:S914–9.

McManis, Bettye, "Eye Screening Program Detects Vision Problems in More than 4,000 Students" *Alabama Education News* (Sep. 1995) 19(1):15.

Milledot, Michel; Lamont, Anne, "Refraction of the periphery of the eye" *Journal of the Optical Society of America* (1974) 64(1):110–111.

Molteno, ACB; Hoare–Nairne, Fraco; Sanderson, GF; Peart, DA; Hodgkinson, IJ, "Reliability of the Otago photoscreener A study of a thousand cases" *Australian and New Zealand Journal of Opthalmology* (1993) 21(4):257–265.

Molteno, A.C.B.; Hoare–Nairne, J.; Parr, J.C.; Simpson, Anne; Hodgkinson, I.J.; O'Brien, N.E.and Watts, S.D., "The Otago Photoscreener, A Method for the Mass Screening of Infants to Detect Squint and Refractive Errors" *Trans. Opthal. Soc. N.Z.* (1983) 35:43–49.

Molteno, A C B; Hodgkinson, I J; Hewitt, C J; Sanderson, G F, "The development of fixing and focusing behaviour in normal human infants as observed with the Otago photoscreener" *Australian and New Zealand Journal of Opthalmology* (1992) 20(3):197–205.

Panescu, D; Webster, JG, Tompkins, WJ; Staley, RL; Johnson, J; Schlageter, D and Stratbucker, RA, "A database of cardiac arrhythmias" *Academic Emergency Medicine* (1995) 2:46–49.

Pujol, Jaume; Arjona, Montserrat; Arasa, Josep; Badia, Victoria, "Influence of amount and changes in axis of astigmatism on retinal image quality" *J. Opt. Soc. Am. A* (1998) 15(9):2514–2521.

Roorda, Austin; Campbell, Melanie C.W., "Geometrical theory to predict eccentric photorefraction intensity profiles in the human eye" *J. Opt. Soc. Am. A* (1995) 12(8):1647–1656.

Roorda, Austin; Bobier, William R., "Geometrical technique to determine the influence of monochromatic aberrations on retinoscopy" *J. Opt. Soc. Am. A* (1996) 13(1):3–11.

Roorda, Austin; Campbell, Melanie C.W. and Bobier, William R., "Slope–based eccentric photorefraction: theoretical analysis of different light source configurations and effects of ocular aberrations" *J. Opt. Soc. Am. A* (1997) 14(10):2547–2556.

Schaeffel, Frank; Weiss, Stefan; Seidel, Jorg, "How good is the match between the plane of the text and the plane of focus during reading?" *Opthal. Physiol. Opt.* (1999) 19(2):180–192.

Seddon, Johanna and Fong, Donald, "A Survey of Vision Screening Policy of Preschool Children in the United States" *Survey of Opthalmology* (1999) 43(5):445–457.

Simons, Brad D.; Siatkowski, R. Michael; Schiffman, Joyce C.; Berry, Barbara E.; Flynn, John T., "Pediatric Photoscreening for Strabismus and Refractive Erros in a High–risk Population" *Opthalmology* 106(6):1073–1080.

Simons, Kurt, "Vision Screening Techniques: A Survey" pp. 56–96.

Tong, Patrick, Y.; Bassin, Roger E.; Enke–Miyazaki, Errin; Macke, Jennifer P.; Tielsch, James M.; Stager, David R.; Beauchamb, George R.; Parks, Marshall M.; The National Children's Eye Care Foundation Vision Screening Study Group, "Screening for Amblyopia in Preverbal Children with Photoscreening Photographs" *Opthalmology* (2000) 107(9):1623–1636.

Wesemann, Wolfgang; Norcia, Anthony M.; Allen, Dale, "Theory of eccentric photorefraction (photoretinoscopy): astigmatic eyes" *J. Opt. Soc. Am. A* (1991) 8(12): 2038–2047.

Williamson, T H; Keating, D, "Telemedicine and computers in diabetic retinopathy screening" *British Journal of Opthalmology* (1998) 82:5.

Prasad, Somdutt; Jones, Karen; Phillips, Russell P. "Telemedicine and computers in diabetic retinopathy screening" *Br J Opthalmol* (1998) 82:849.

Wooton, Richard, "Telemedicine: a cautious welcome" *BMJ* (1996) 313:1375–1377.

* cited by examiner

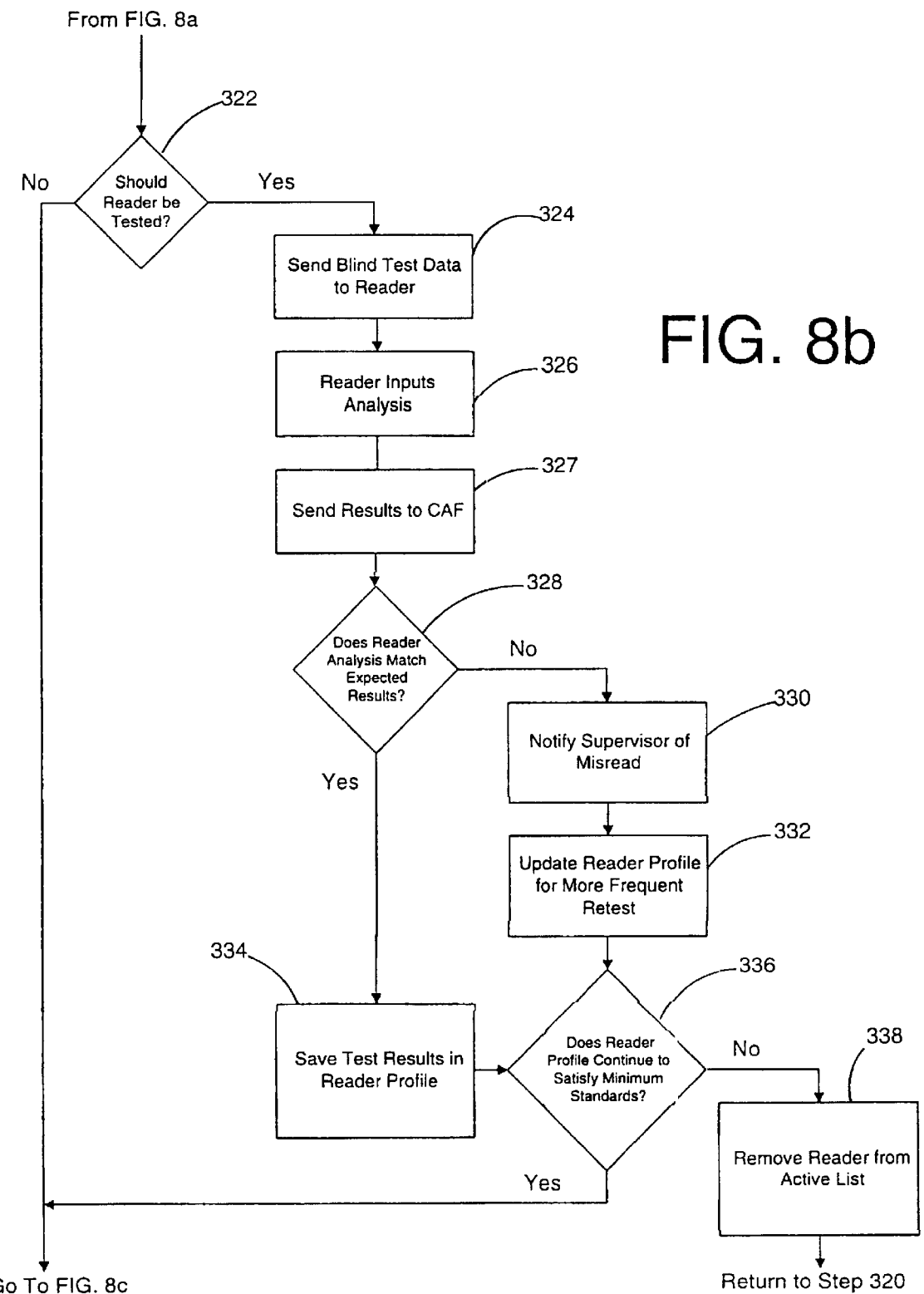

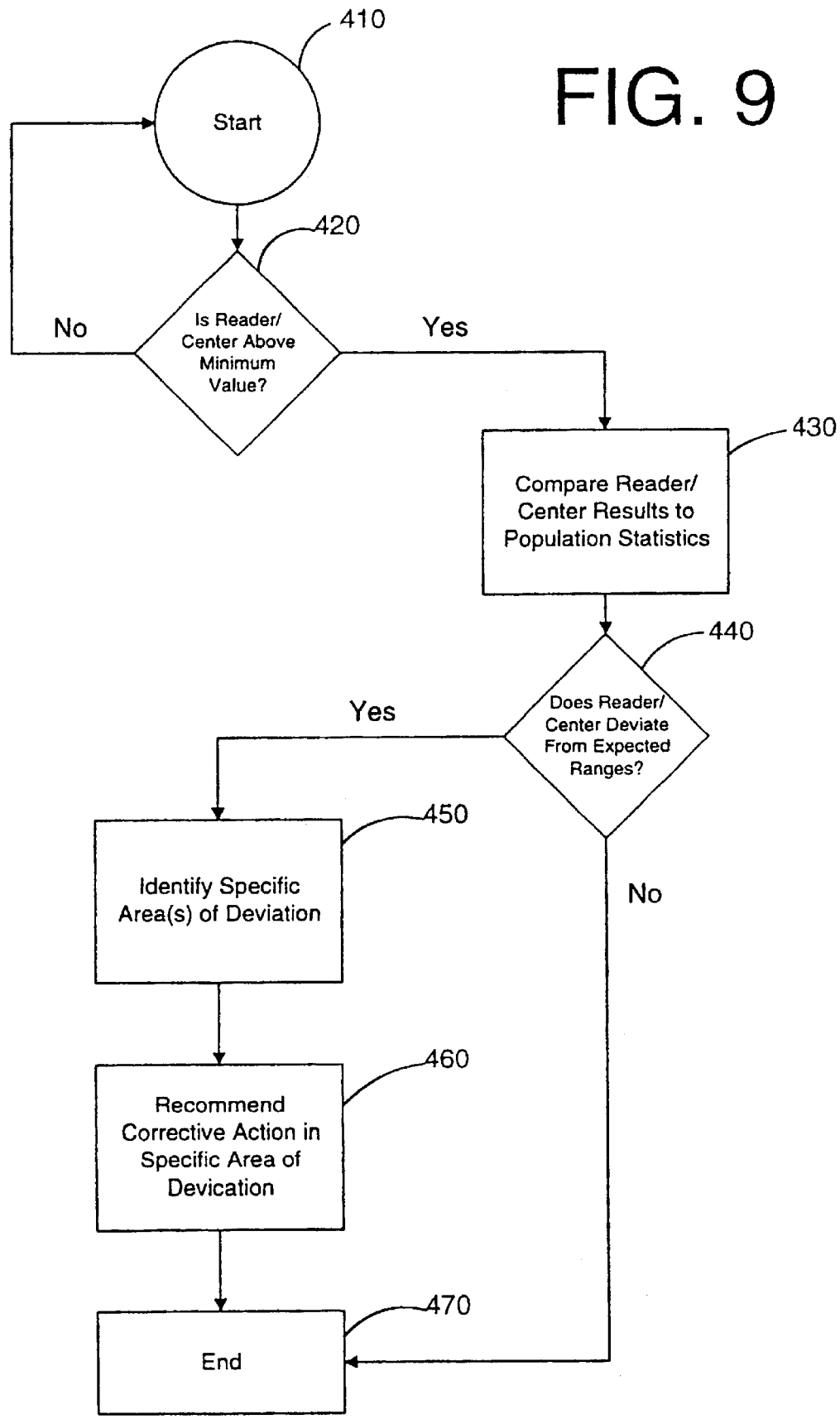

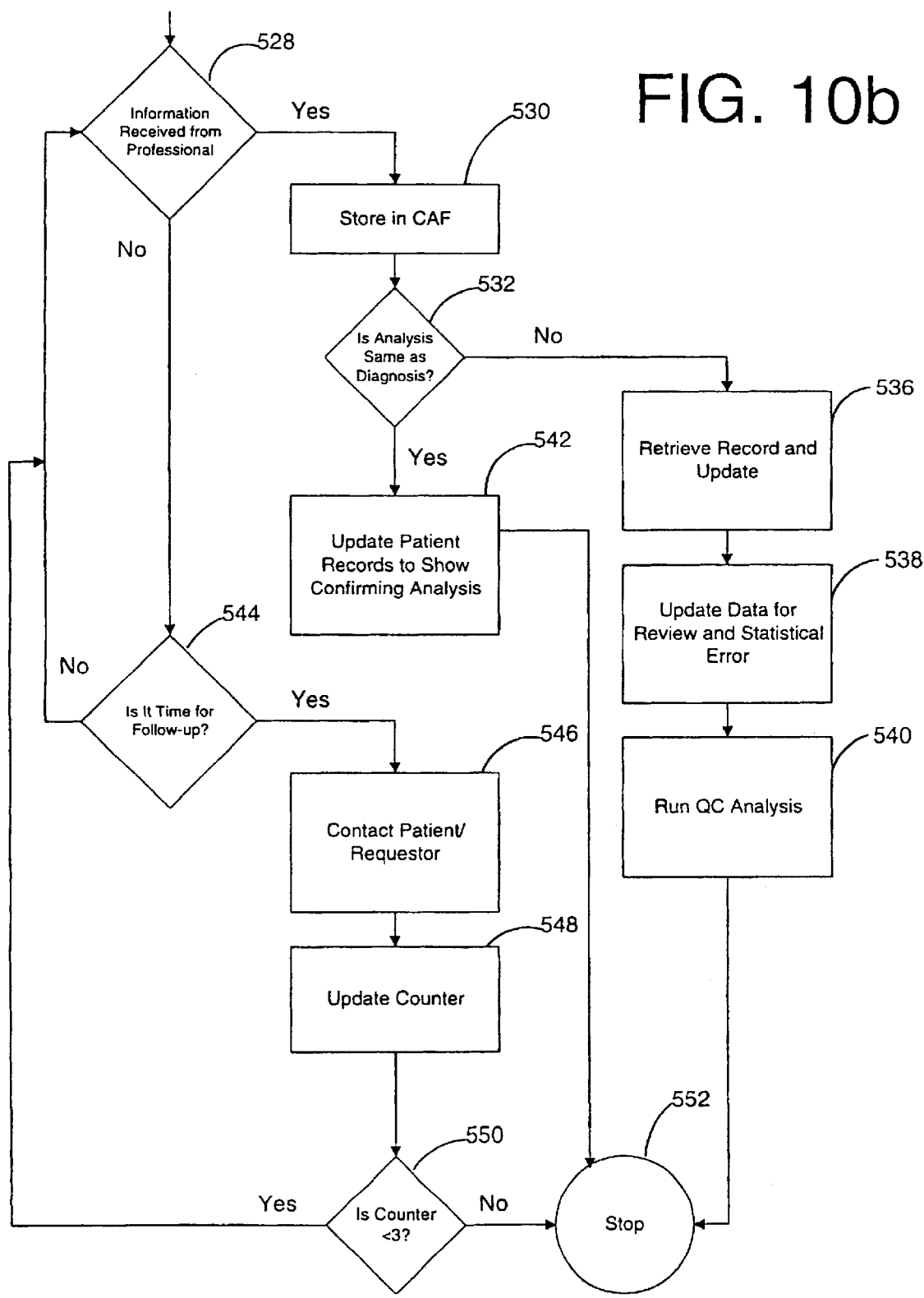

SYSTEM AND METHOD FOR EYE SCREENING

FIELD OF THE INVENTION

The present invention relates to methods and systems for screening eyes for indications of abnormalities. In a preferred aspect, the invention is configured for specific application to screening of preschool and school-age children to provide detection of ocular disease, abnormalities and conditions that may lead to amblyopia. Further, the present invention has application for general vision screening to detect vision problems.

BACKGROUND OF THE INVENTION

Detection of ocular disease and abnormalities in preschool children is important to prevent long-term vision impairment. During early development, the child's brain attempts to process visual information that is received in both of the child's eyes. However, if an ocular malady or impairment exists in one of the child's eyes which goes untreated for an extended period of time, the brain eventually stops processing information from the diseased eye, and leads to the severe ocular condition of amblyopia. Detection and treatment of amblyopia is required at an early stage of childhood development before the condition becomes irreversible.

While early detection of ocular disease and abnormalities in preschool and schoolage children is desirable, the ability of an ophthalmologist, pediatric ophthalmologist, optometrist, pediatrician, family practitioner, or other trained health care worker, henceforth collectively called health care professional, to identify certain eye maladies in young children is complicated by the age of the child, and in many cases, the inability of the child to communicate with the health care professional. Common diseases and abnormalities which must be detected and treated in children include misalignment of the optical axes of the eyes (strabismus), refractive errors which include nearsightedness (myopia), farsightedness (hypermetropia), astigmatism, and anisometropia (unbalanced refraction), opacities (like cataracts) and other conditions which reduce vision.

In the past, ocular screening of a patient's eyes has been done manually where a physician observes reflections from a hand-held light source, and more recently by observing recorded images of the patient's eyes on conventional film (35 mm or Polaroid®) or a charged coupled device (CCD). In the case of recorded images, a flash beam of light is positioned to travel off of, but nearly coincident with, an optical axis defined by the camera. The incoming flash beam of light is refracted by the cornea and lens of the patient's eye and falls generally on the pigmented macula and fovea of the patient's retina. An image of the illuminated retina, called the retinal reflection or retinal reflex, is recorded by the camera. A portion of the incoming light is reflected from the front of the cornea as a corneal reflection or corneal reflex. Additionally, a picture of the area around the eyes (eye lids and orbital structure) is recorded by the camera. The recorded image is stored for later evaluation by a health care professional trained in the art of vision screening. Based on an evaluation of the corneal and retinal reflections, which may take days or even months to develop and review, the health care professional is able to identify certain ocular maladies.

The benefits of vision screening for young children has been long recognized. However, such screening is not cost effective on a wide scale if conducted by professionally trained eye care specialists, such as optometrists and ophthalmologists. In an effort to identify young children demonstrating risk factors associated with common ocular diseases and abnormalities, mass screening programs have been attempted.

At least one goal of these screening programs is to provide a cost effective and accurate screening for certain eye maladies. Additionally, the false negative results of the screening process must be maintained within a narrow range to limit the number of children who are improperly assured no vision problems exist. Further, false positive results must also be minimized to limit unnecessary referrals to medical professionals. At least one report on prior eye screening programs cautions that an overreferral pattern of "normal" patients could flood the health care system and misappropriate health care dollars.

Early efforts at creating effective eye screening relied on a manual review of Polaroid® type photographs of children's eyes. A study has evaluated the MTI photoscreener in a patient population of 15,000 children aged 6 to 47 months. A relatively high percentage of children (nearing 5%) had photographs taken that could not be used for photoscreening. Thus, these individuals received no benefit from the screening process. Further, the study reported that only 60% of those children with a positive screening result actually had an eye disorder diagnosed after a follow-up examination. An additional factor, and potentially more significant for patient health, was that assuming amblyogenic factors are present in approximately 5% of the population, the reported photo screening method missed as many children with these factors as they identified. The lack of quality assurance inherent in these types of photo screening methods has led to criticism since there is a high degree of subjectivity and interobserver variability leading to unacceptable levels of false negative and false positive test results.

Notwithstanding the advancements made in the prior art in the field of ocular screening for children, there is a need for an ocular disease and abnormality detection method which improves the accuracy and reliability of the screening process. The screening process should also be cost effective for wide scale application and use.

SUMMARY OF THE INVENTION

One object of the present invention is to provide a method for accurate screening of eye images to detect abnormalities and disease. In one aspect of the invention, an image of an eye is obtained and digital data corresponding to that image is transmitted to a central facility. Through an automated process, the central facility selects a qualified reader and transmits the image data to the reader for review and analysis. The reader inputs their analysis of the patient eye image and transmits that information electronically to the central facility. The central facility automatically tabulates the readers analysis and generates a report which is then transmitted to the patient. In a preferred aspect of the invention, the reader is periodically tested to assess skills and accuracy of reading images demonstrating known patterns of ocular disorders. Further, in a still more preferred aspect, the central facility routinely evaluates reader results and compares these results to expected results based on statistical assumptions to determine if reader results are within acceptable margins.

In still a further aspect of the invention, a method is provided for screening of patients for ocular disease and abnormalities at locations remote from skilled analyzers trained to interpret eye images. This method includes providing a remote site with a photoscreening device for generating images of corneal and retinal reflections from a patient eye and a device for recording such images. An image of the eye including corneal and retinal reflections is obtained and the information is transmitted to a central data facility. The central data facility automatically selects an analyzer for evaluating the image of the patient's eye. The digital information of the patient's eye is transmitted to the image analyzer. In a preferred aspect, the image of the patient's eye is accompanied by a standardized form which may be easily completed by the analyzer to insure consistent descriptions of the observed abnormalities. Information related to the presence of abnormalities in the patient's eye is generated and the information is transmitted back to the central data facility. The central data facility may then provide the patient or requester with the results of the screening. In a preferred aspect, the prior accuracy or educational level of the analyzer is considered by the central data facility and if a minimum threshold is not met, the patient's information will be transferred to a second analyzer to obtain a second opinion. In still a further preferred aspect, a percentage of each of the images reviewed are forwarded to second reviewer for a second opinion. The percentage of images sent for second opinions may be controlled to vary depending on reviewer training and accuracy demands. In this preferred aspect, the first reader's analysis and the second reader's analysis are compared and if identical the information will be transmitted to the central data facility and on to the patient. However, if discrepancies are detected, the method may resolve the inconsistencies prior to sending the results to the patient.

In a further aspect of the invention, a system is provided for eye screening. The system comprises a remote data entry device and eye image acquisition device. At least one of the devices is electronically connected to a central data facility. The central data facility may be electronically connected to a plurality of remote readers.

These and other objects of the present invention. will become apparent from the following figures and description of the preferred embodiments.

BRIEF DESCRIPTION OF THE DRAWINGS

FIGS. 8a–8d are flowcharts setting forth a method of eye screening according to the present invention.

FIG. 9 is a flowchart demonstrating a method of quality control according to the present invention.

FIGS. 10a–10b are flowcharts setting forth a follow-up method according to another aspect of the present invention.

DESCRIPTION OF THE PREFERRED EMBODIMENTS

Figure 1:
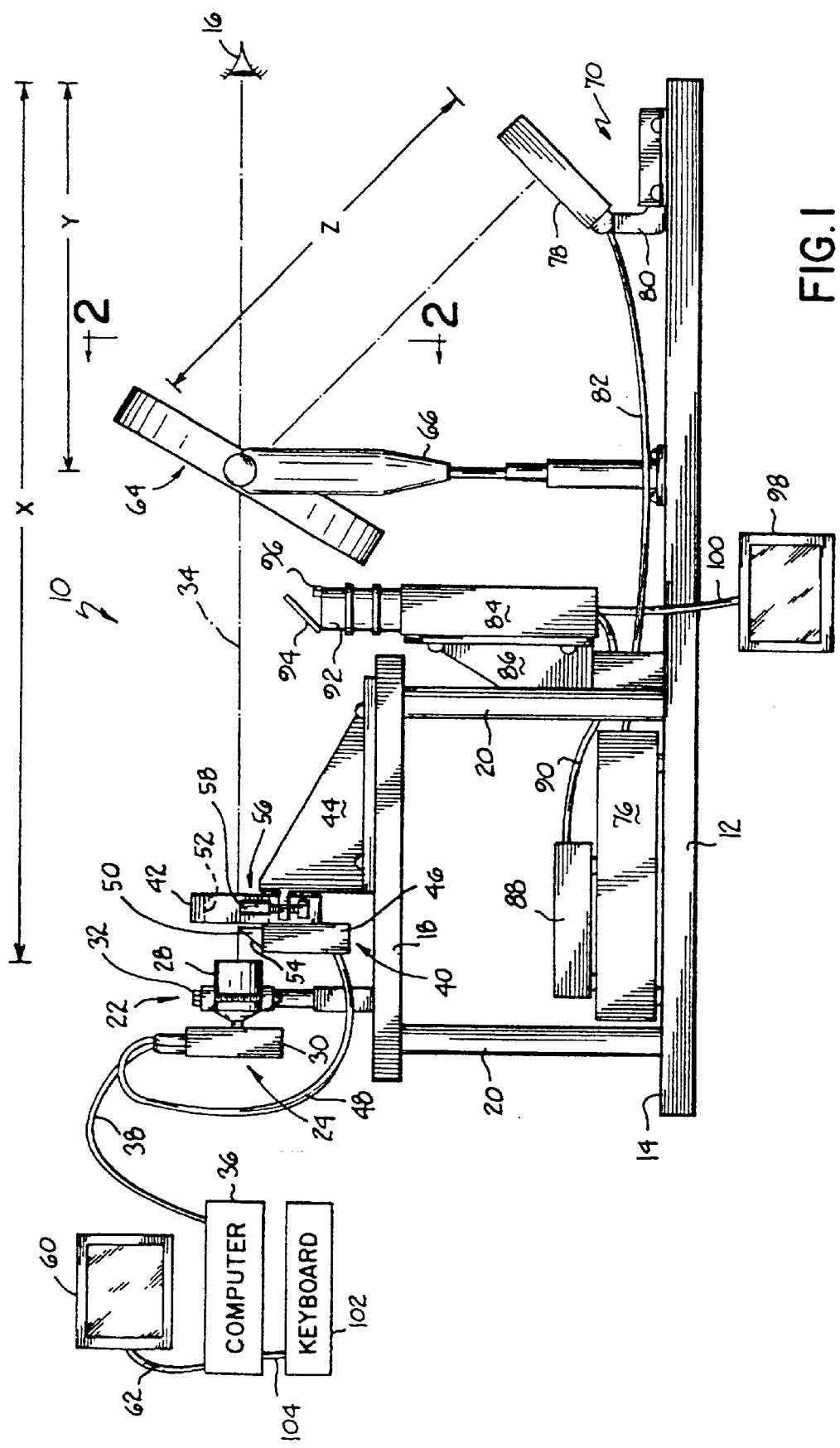
FIG. 1 is a side elevation view of an ocular disease and abnormality detection device in accordance with the principles of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device and methods, and such further-applications of the principles of the invention as illustrated therein being contemplated as would normally occur to one skilled in the art to which the invention relates.

With reference to the figures, and to FIG. 1 in particular, an ocular disease and abnormality detection device 10 is shown in accordance with the principles of the present invention. Ocular disease and abnormality detection device 10 is particularly adapted for use by health care professionals or photoscreening technicians to identify various diseases or abnormalities which can occur in a patient's eyes. The various eye diseases and abnormalities which may be detected by the present invention include, by way of example and without limitation, misalignment of the optical axes of the eyes (strabismus), refractive errors which include nearsightedness (myopia), farsightedness (hypermetropia), astigmatism and anisometropia (unbalanced refraction), occlusions (like cataracts) and other conditions that reduce vision. As will be described in more detail below, ocular disease and abnormality detection device 10 is adapted to generate a flash beam of light toward a patient's eyes, and to record and display corneal and retinal reflections of the patient's eyes for immediate or future evaluation by the health care professional. Based on the characteristics of the corneal and retinal reflections, various diseases and abnormalities in the patient's eyes may be readily identified.

As shown most clearly in FIG. 1, ocular disease and abnormality detection device 10 includes, in one embodiment, a rigid horizontal platform 12 which is adapted to provide a level support surface 14 above a floor (not shown) for mounting various components of the detection device 10. At one end of detection device 10, remote from a patient's eyes 16 (one shown), a raised horizontal platform 18 is mounted on vertical support member 20 which extends upwardly from the support surface 14. A clamp assembly 22 is mounted to the raised platform 18 for supporting a photo-imaging device 24 which is used to record corneal and retinal reflections. 26 (FIGS. 3–6) of the patient's eyes 16 during the ocular disease and abnormality detection procedure as will be described in detail below.

Photo imaging device 24 preferably includes an optical lens 28 which is attached to body 30 of the photo-imaging device 24 by conventional C-mount. Clamp assembly 22 includes a holding bracket 32 adapted to securely hold the optical lens 28 in alignment with an optical axis 34 which is coincident with the position of the patient's eyes 16. Lens 28 of photo-imaging device 24 is spaced-from the patient's eyes 16 a predetermined focal distance "X", and preferably faces the patient's eyes 16 for receiving the corneal and retinal reflections. Operation of photo-imaging device 24 is preferably controlled by a computer 36 which is coupled to the photo imaging device 24 through a cable 38. In a preferred aspect, computer 36 includes one or more processors and memory for data storage. The computer sends command signals to the photo-imaging device 24, and the photo-imaging device 24 sends recorded corneal and retinal reflections 26 from the patient's eyes 16 to the computer 36.

In accordance with the present invention, the photo-imaging device 10 preferably comprises a color digital camera which is adapted to electronically record the corneal and retinal reflections 26 (FIGS. 3–6) from the patient's eyes 16. While a color digital camera is preferred, it is contemplated that other photo-imaging devices, such as a standard color or greyscale film camera (35 mm or Polaroid®) or other digital cameras like a charge coupled device (CCD) are possible without departing from the spirit and scope of the present invention.

As shown most clearly in FIG. 1, a flash unit 40 and ring body 42 are also supported on raised platform 18 through a bracket 44. Flash unit 40 includes a vertically adjustable flash device 46 which is coupled to photo-imaging device 24 through cable 48 for receiving a flash command from the photo-imaging device 24. Flash device 46 is preferably mounted off the optical axis 34 for generating a flash beam of light upwardly on a vertical axis transverse to the optical axis 34. A right-angle prism 50 is supported on the flash device 46 for directing the flash beam of light an aperture 52 in ring body 42 and toward the patient's eyes 16. Prism 50 turns the flash beam of light form the upward direction on the vertical axis to align generally with the optical axis 34. Surface 54 of prism 50 is preferably painted with an opaque material to prevent transmission of light from flash device 46 to the lens 28 of photo-imaging device 24.

The flash beam of light generated by flash device 46 produces corneal and retinal reflections 26 from the patient's eyes 16 (FIGS. 3–6) which are recorded by photo-imaging device 24 and preferably received and stored in computer 36. A color video display screen 60 is preferably coupled to computer 36 through cable 62 for displaying selected color corneal and retinal reflections 26 from a patient's eyes 16.

As shown in FIG. 1, a substantially transparent pellicle beamsplitter 64 is pivotally supported on an adjustable stand 66 mounted to the support surface 14 and spaced a predetermined focal distance "Y" from the patient?s eyes 16. Beamsplitter 64 is preferably positioned on optical axis 34 intermediate the photo-imaging device 24 and an adjustable headrest which is provided to support the patient's head in a fixed position and align the patient's eyes 16 on the optical axis 34. Beamsplitter 64 is made of a thin membrane, such as MYLAR or similar material, and is preferably about 92% light transmissive and about 8% reflective. In accordance with the present invention, beam splitter 64 is operable to pass the flash beam of light from flash device 46 to the patient's eyes 16, and to pass the corneal and retinal reflections 26 from the patient's eyes 16 to the lens 28 of photo-imaging device 24. To accommodate for light transmission loss through the beamsplitter 64, the brightness of the flash beam of light generated by flash device 46 is preferably adjustable to an acceptable brightness level.

As shown in FIG. 1, a visual stimulus generator 70 may be provided to assist in focusing the patient's eyes 16 on the lens 28 of photo-imaging device 24 during the ocular disease detection procedure of the present invention. Visual stimulus generator 70 is spaced a predetermined focal distance "Z" form beamsplitter 64, and is operable to project a visual image 72 (FIG. 2) on a surface 74 of the beamsplitter 64 which faces the patient's eyes 16. The sum of the focal distances "Y" and "Z" preferably equals the focal distance "X" such that the projected image 72 appears to the patient's eyes 16 as being aligned on the optical axis 34 and generally superimposed on the lens 28 of photo-imaging device 24. By superimposing the projected image 72 on the lens 28 of photo-imaging device 24 during the ocular disease and abnormality detection procedure of the present invention, the patient's eyes 16 generally focus on lens 28 to permit accurate corneal and retinal reflections 26 of the patient's eyes 16 to be recorded by the photo-imaging device 24.

Figure 2:
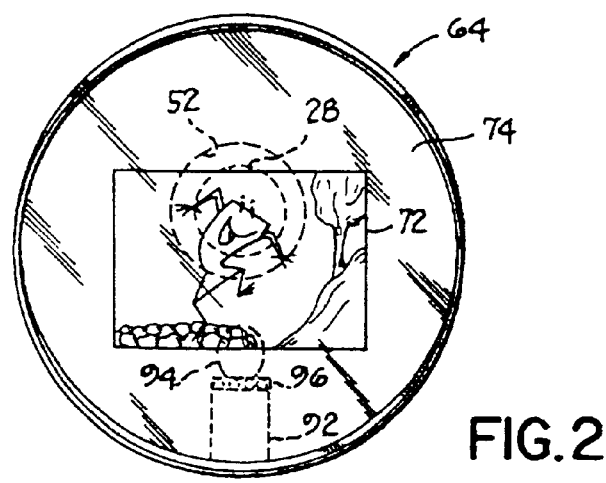
FIG. 2 is a schematic view showing a patient's view of the ocular disease and abnormality detection device of the present invention, taken along line 2—2 of FIG. 1.
Figure 3:
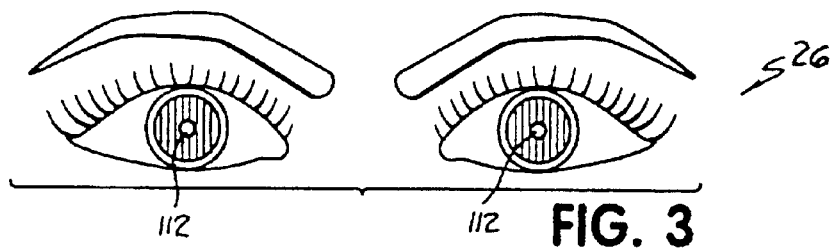
FIGS. 3–6 are illustrations of eyes of patients recorded by the ocular disease and abnormality detection device of the present invention.
Figure 4:
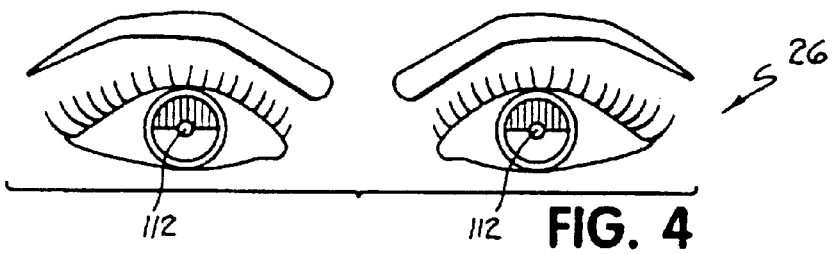
Figure 5:
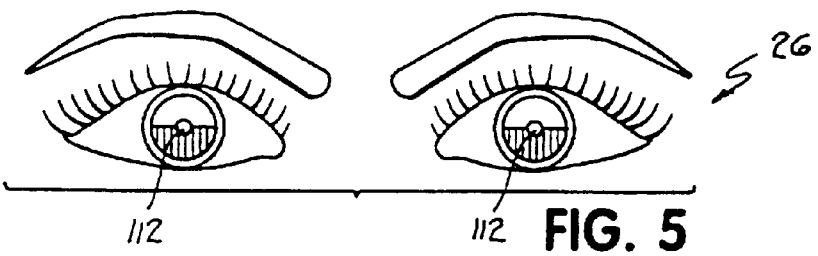
Figure 6:
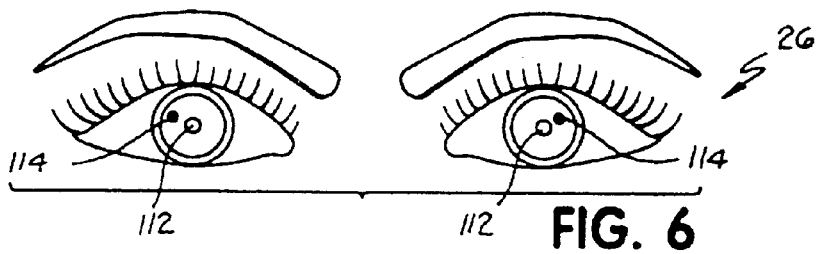

Still referring to FIGS. 1 and 2, visual stimulus generator 70 preferably includes a video display device(VDD) 76 which is adapted to generate moving visual images 72 (FIG. 2) from a video storage device.(not shown). A flat video display screen 78 is pivotally supported on a stand 80 mounted to support surface 14. Video display screen 78 is coupled to the video display device through cable 82 for projecting the moving visual images 72 on the surface 74 of beamsplitter 64 The moving visual images 72, such as animated cartoons, are preferably selected to draw and keep the attention of a preschool patient during the ocular disease detection procedure of the present invention. It will be appreciated that other devices for projecting a visual image on surface 74 of the beamsplitter 64 are possible without departing from the spirit and scope of the present invention. For example, visual stimulus generator 70 could include a video laser disc player, a digital video disc player, a computer for generating images in retrograde fashion, or a standard image projector as will be appreciated by those skilled in the art. Preferably, one or more speakers (not shown) are connected to the video cassette player 76 and positioned near photo-imaging device 24 to further attract the child's eyes to the camera lens 28.

Referring to the embodiment of FIG. 1, the ocular disease and abnormality detection device 10 includes a greyscale video camera 84 which is mounted to the support surface 14 through a bracket 86. A power supply 88 is coupled to video camera 84 through cable 90. Video camera 84 is mounted off the optical axis 34 and includes a lens 92 for viewing the patient's face during the ocular disease and abnormality detection procedure of the present invention. In a preferred embodiment, a series of infrared light emitting diodes (LED's) 96 are mounted on the lens 92 of video camera 84 and directed toward the patient's face to illuminate the patient's face for this purpose. Infrared light emitted from the LED's 96 is not visible to the patient's eyes 16, but the video camera 84 may be sensitive in the IR wavelength to provide images of the patient's face. A video display screen 98 is coupled to the video camera 84 through cable 100 for displaying real time images of the patient's face to the health care professional or photoscreening technician. By viewing the patient's face in the video screen 98, the health care professional or photoscreening technician can quickly check the patient's eyes 16 both for alignment and pupil dilation before corneal and retinal reflections of the patient's eyes 16 is recorded by the photo-imaging device 24. Preferably, the brightness of the visual image 72 projected by the visual stimulus generator 70 is adjustable to permit pupil dilation of the patient's eyes to be adjusted. The health care professional or photoscreening technician can readily increase or decrease the patient's pupil size by decreasing or increasing the brightness of visual image 72, respectively.

Figure 7:
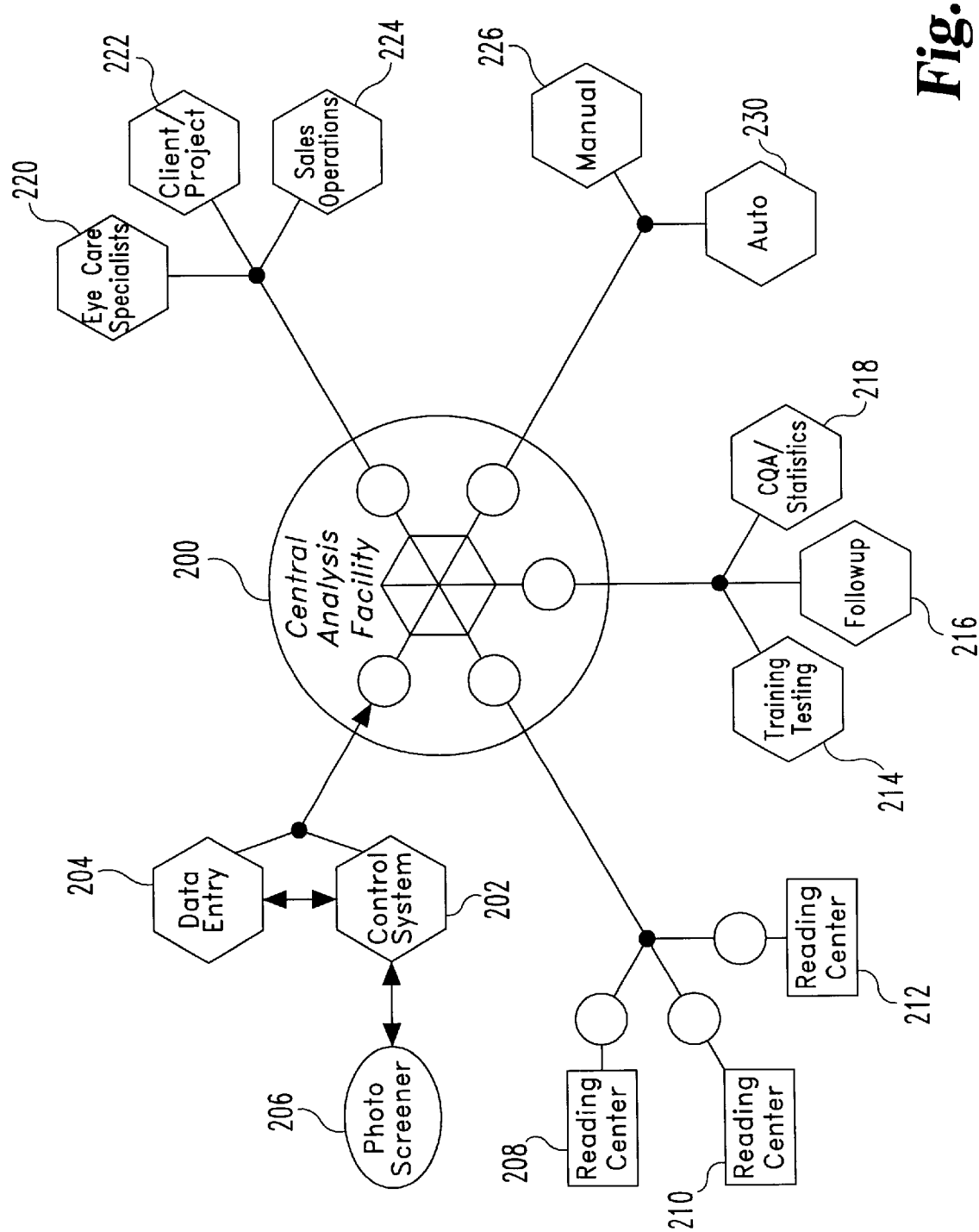
FIG. 7 is a block diagram of a system for eye screening according to the present invention.

The present invention is directed to utilizing and analyzing visual information concerning ocular health. More specifically, the present invention is directed to improved methods of analyzing patient information to develop accurate indications of eye abnormalities. Referring now to FIG. 7, there is shown a system for eye screening according to the present invention. At the core of the system is a central analysis facility 200 (CAF). Central analysis facility 200 may include a number of processing elements, databases, external communication devices, input devices and display devices. Preferably, central analysis facility 200 has the ability to exchange electronic data between a number of remote facilities. The exchange of information may be conducted by any known techniques which may include direct interconnection between the remote sites, local area networks, intermittent connections including dial-up, satellite, or other types of connections. Furthermore, the information may be exchanged via one or more internet service providers. More specifically, remote users may be able to access an internet web site supported by the central analysis facility and download relevant information. In a like manner, these users may be able to transmit their information via the internet to the central analysis facility.

A remote site for gathering patient information is provided and includes a control system 202 having at least one processor and preferably including sufficient memory to store patient data. Patient data may be entered through data entry device 204. This may include, but is not limited to, manual keyboards, bar code readers, scanners, video imaging systems, or any other means to enter data into the system. Furthermore, the data entry device 204 may include a connection to a database containing patient data and the control system 202 may receive the data and populate a database designed for use with the present invention. Finally, a photo screener 206 may be utilized to obtain a patient eye image. In a preferred aspect, that information is transmitted to the control system 202 for relation to the patient information previously entered by device 204. In a preferred system, a duplicate copy of the patient data would be embedded in the corresponding photo screener image. Photo screener 206 may be similar to that previously described with respect to FIG. 1, but may have more or less features than that previously described without deviating from the spirit and scope of the present invention. Further, photographs generated by other eye imaging devices may be scanned into an electronic format and input into the system of the present invention.

As will be described more fully below, information from the control system 202 or data entry 204 may be transmitted to the central analysis facility 200. While only one control system 202 and central analysis facility 200 are shown with the present invention, it is contemplated that a plurality of remote data entry devices and central analysis facilities may be used with the present invention. Further, it is contemplated that remote control system 202 may be located in a foreign country to assist in vision screening programs in less developed areas of the world. In a preferred aspect, central analysis facility 200 may automatically select one or more reading centers designated as reading center 208, 210 or 212. While only three reading centers are shown for the purpose of illustration, multiple reading centers or individual readers may be continuously or intermittently electronically connected to CAF 200. Patient data may be electronically transmitted from the central analysis facility to any of the reading centers using known communications techniques. Further, central analysis facility 200 may be electronically connected to a training and testing database 214, a follow-up database 216 and continuous quality assurance and statistics module 218. It is contemplated that these databases and modules may be a part of the central analysis facility or may be remote from the facility without deviating from the present invention. The present invention further contemplates optional electronic connections between the central analysis facility and eye care specialist 220 and the client/project coordinator 222. Data from the screening process may be electronically transmitted to either one or both of the eye care specialist 220 or the client/project coordinator 222. Further, follow-up data may be transmitted back to CAF 200 from the remote sites.

It is also contemplated that sales and operations personnel may have access to the central analysis facility 200 to coordinate the movement of data, evaluate the status of projects or clients, and generally review information available at the central analysis facility. Finally, technical support may be provided to the central analysis facility 200 via manual connection 222 or an automatic module 230. It is contemplated that requests for technical support of the automated system may come from any of the previously described users or groups connected to the CAF 200. Furthermore, either manually or automatically, the system may be directed to update system parameters or software for any of the users when they contact the central analysis facility 200. The operation of the various components of the eye screening system described above are described more fully as follows.

Referring to FIGS. 8a–8d, there is shown a preferred embodiment of a method for analyzing patient information according to at least one aspect of the present invention. The method starts at step 300 and may include initializing the system, starting hardware and peripheral instruments, calibrating the system and obtaining any system upgrades. After the necessary components have been initialized and the system is operational, information about the patient is entered into the system at step 302. Such information may include, but is not limited to, patient identification (name, social security number, study number) and background information (age, race or ethnicity, contact information, etc.). As described above, the system may include a keyboard or touch screen which will allow a user to input patient information directly into the system. Furthermore, it is contemplated that additional input devices such as bar code. readers, scanners (with or without optical character recognition), voice. recognition software, or any other convenient input devices may also be used in conjunction with this system. A further feature of a system according to the present invention may allow the input of the patient information in step 302 to be accomplished by database access and download. Specifically, it is contemplated that much of the necessary patient information may be obtained from public and/or private computer database records in which case this information may be directly downloaded to the system via an automated process.

Once the patient information of step 302 has been input into the system, shown in FIG. 7, an image of the patient's eye or eyes is obtained in step 304. In a preferred aspect of the invention, the image is a photoscreening image generated with an apparatus adapted to generate a flash and record a digital image of an eye or eyes. The system may also be used with conventional photo screening devices. For example, a photo from an imaging device may be scanned or otherwise digitized for input into the system of the present invention. The image may be of a binocular view, a monocular view or a composite image generated from multiple exposures. Furthermore, the eye image may contain multi-spectrum images or may have multiple images generated from various spectral light sources. In another preferred step, the method determines in step 306 whether the eye image that was obtained in step 304 has characteristics that would make it readable by an analyst to detect abnormalities or disease. In a preferred aspect, the operator of the apparatus shown in FIG. 1 views the eye image on display 60 and verifies that the appropriate image or images have been obtained. It is also contemplated that a software algorithm may evaluate the eye image and provide feedback to the operator on the quality of the image. If a qualifying image has not been obtained, the method would return to step 304 and a new image of the eye would be obtained.

Assuming that the image of the eye is deemed readable, the method progresses to step 308 where the image data is saved in a machine readable format. Although step 308 references storing the information locally as an optimal choice this step is not required and data may be directly transferred to the CAF. Without limiting the method of the present invention, it is contemplated that the data would be in a digital format. Further, it is preferred that the patient information obtained in step 302 is related to the acquired image data.

The steps 302–308 may be repeated any number of times to screen a large population of patients. More specifically, it is anticipated that an entire school, pre-school, daycare center, church, or other group of individuals may be screened in a single setting with the data maintained in machine readable format by control system 202. Alternatively, individual children may be screened in a pediatrician or primary care physician's office with the data maintained in machine readable format by the control system 202. As shown in step 310, the data of either a single patient or a plurality of patients is then sent to the central analysis facility (CAF). As shown in step 311, the data is then saved in the central analysis facility (CAF) to preserve a record of the information. It will be appreciated that step 310 may be performed after the acquisition of each image in steps 304–308 or may be commenced on a periodic basis; The download of information may occur to free-up data storage facilities or may be conducted, for example, nightly via remote access. In a preferred aspect, data would be stored for an entire day of screening and the system would then be accessed remotely during non-working hours and the information downloaded to central analysis facility 200.

The central analysis facility stores the patient data in a database to preserve the information. After the information has been saved in step 311, the system determines in step 312 whether the patient is participating in a particular project. It will be understood that in a preferred aspect, a state or other organization may fund a screening project for their citizens or members of their organization. As a part of this funding, the sponsoring organization may require that the actual screeners of the patient images be conducted by a selected group of screeners. More specifically, for example, a state may mandate a screening of all individuals below the age of 6 within the state and may require that the screening program utilize certified screeners associated with universities sponsored by the same state. Thus, the sponsoring organization mandates that these images be screened by only those individuals associated with other state organizations. In the present method, as a preferred aspect, the methodology anticipates this request and inquires in step 314 whether the project requires designated readers. If a project requires designated readers, then, as shown in 316, the central analysis facility examines only queues for designated readers and in step 320 selects an appropriate reader to receive the data. If the project does not require designated readers, then the methodology moves forward to step 318 where the entire of array of available readers is accessed to determine their availability. As shown in step 320, an appropriate reader is selected from the available readers.

The terms screeners, readers, and analyzers are used synonymously throughout his application and refer generally to individuals trained to view images of patient's eyes, and evaluate those images for signs of disease, abnormalities, or impaired vision. More specifically, the system analyzes the queue of each of the readers and/or reading centers and determines which one has availability. Further, individual readers and reading centers having multiple readers may be evaluated in a similar manner by the system. The information may then be routed to the reader with the lowest queue value. The system may be calibrated to send single records of patient information or blocks of information, for example, 50 or 100 patient records. Criteria for selecting a reader may include a number of factors, but, accuracy, availability and time to turnaround analysis may be critical factors. It is contemplated that each time a patient record is sent to a reviewer, a corresponding counter or queue is updated. Similarly when an analysis is returned by a reader, the queue is updated. The time between sending the request for review and return of analysis may be recorded. This information is preferably utilized by the central analysis facility as a criteria to select the next available reader.

As described in the background of the application, previous systems have had difficulty assuring the quality of readings and have not been widely adopted because of the large number of errors in reading the images either in a purely automated system or manual review of physical images. Referring to FIG. 8b, in a preferred aspect of the present invention, the system determines if a reader selected in step 320 should be sent a test sequence to evaluate effectiveness. Referring to step 322, this process may include a randomized systematic sampling of all readers qualified to receive data as well as a heightened selectivity for those readers which have not been fully certified for independent reading of patient images. Further, individual readers or reading centers may have experienced difficulty identifying various abnormalities. In one aspect of the present invention, reader and/or reading center results are compared to expected averages. Through this, readers having statistical averages above the standard deviation of the expected population will be targeted for follow-up testing. If a designated reader or center is determined to need testing, then in step 324 blind test data is electronically recalled from testing database 214 and transmitted to the designated reader. The blind test data may contain one or a series of images with a diagnosis or analysis agreed upon in advanced to test the readers ability to recognize various indices of abnormalities. As shown in step 326, the reader inputs their analysis of the image or images, the data is then associated with the original blind test data and the analysis and data, hereinafter the analysis, is sent to central analysis facility in step 327. The central analysis facility then compares the conclusion reached by the reader with the results expected for the test images. In a preferred aspect, the reader inputs their analysis into a pre-defined format such that the information may be easily tabulated and compared with the blind test data expected results that are stored in a similar format. Thus, in a preferred aspect, the comparison in step 328 may be conducted in an automated fashion by the central analysis facility. It is contemplated that while in a preferred aspect the central analysis facility utilizes automated processing units to make the comparison, the comparison may be performed manually to achieve a further level of review.

If the results of the reviewer do not match the expected results, a supervisor is notified of the misreading of the blind test data in step 330. As shown in step 332, the reader's profile is updated to indicate the misread of the blind test data. This information in the reader's profile may be utilized to formulate a more frequent test schedule of the reader missing the blind test data or that further training is required. If the reader's analysis matches the expected results, as shown in step 334, the results from the blind test data are saved to the reader's profile. Again, this information may be utilized to suggest less frequent testing of the reader if they continue to demonstrate proficiency in reading patient images.

The reader profile may include various factors for accuracy including accuracy on blind test data, previous training completed, statistical deviation from expected norms, initial screening analysis that are later proven accurate by eye care specialists like optometrists or ophthalmologists. In step 336, the system analyzes the reader profile and determines if it continues to meet minimum standards for readers. As explained more fully below, these standards may be adjusted to satisfy requirements of a particular project as well as improve overall efficiency and efficacy of the screening system. If the screener no longer satisfies these minimum standards, in step 338 the reader is removed from the active lists of readers who may be assigned patient images to review. At this point, the system would then return to step 320 and attempt to designate a new appropriate reader. If the reader continues to demonstrate satisfaction of the minimum standards, the patient data is sent to the reader in step 340.

Figure 8A:
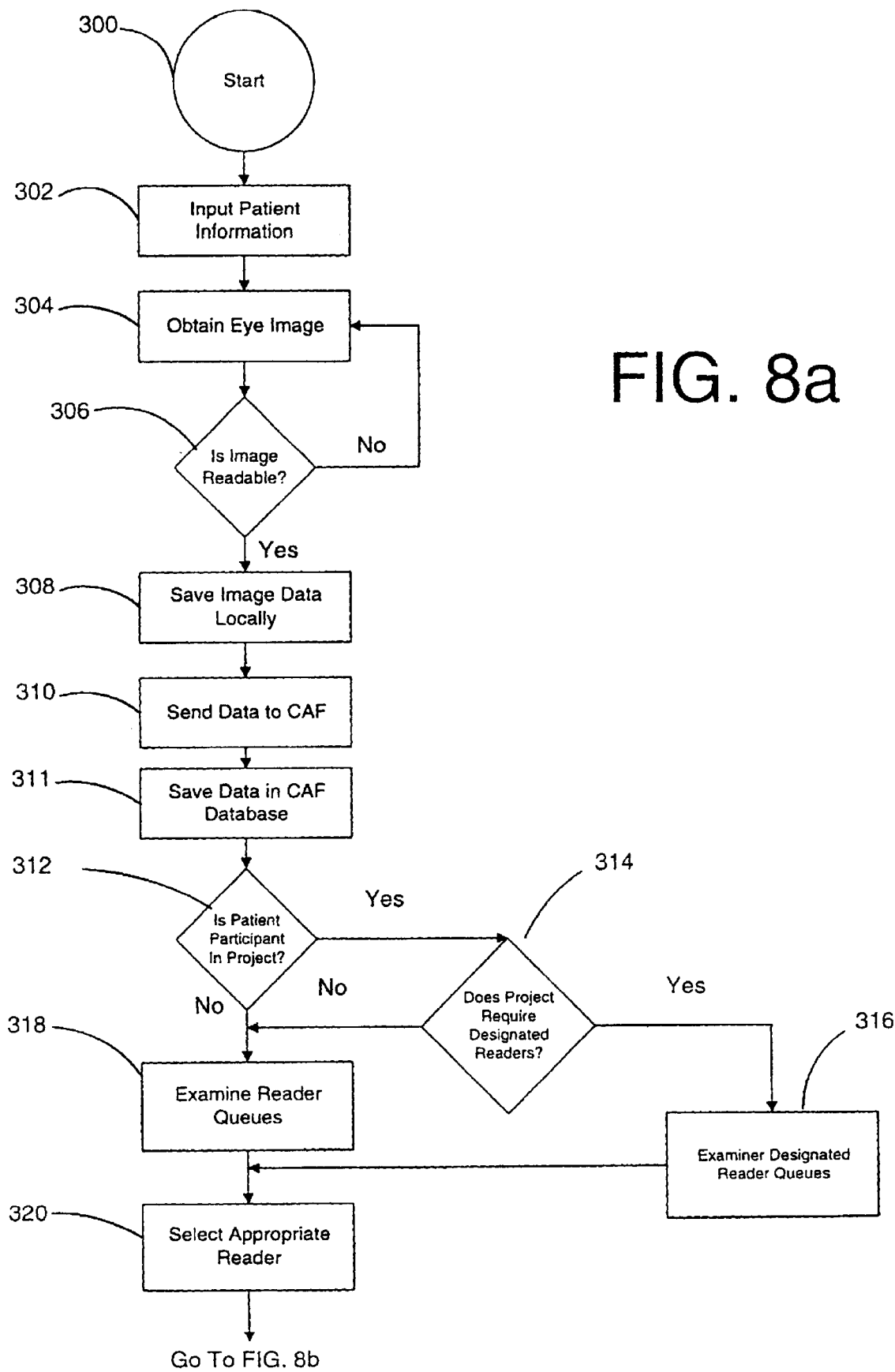
Figure 8C:
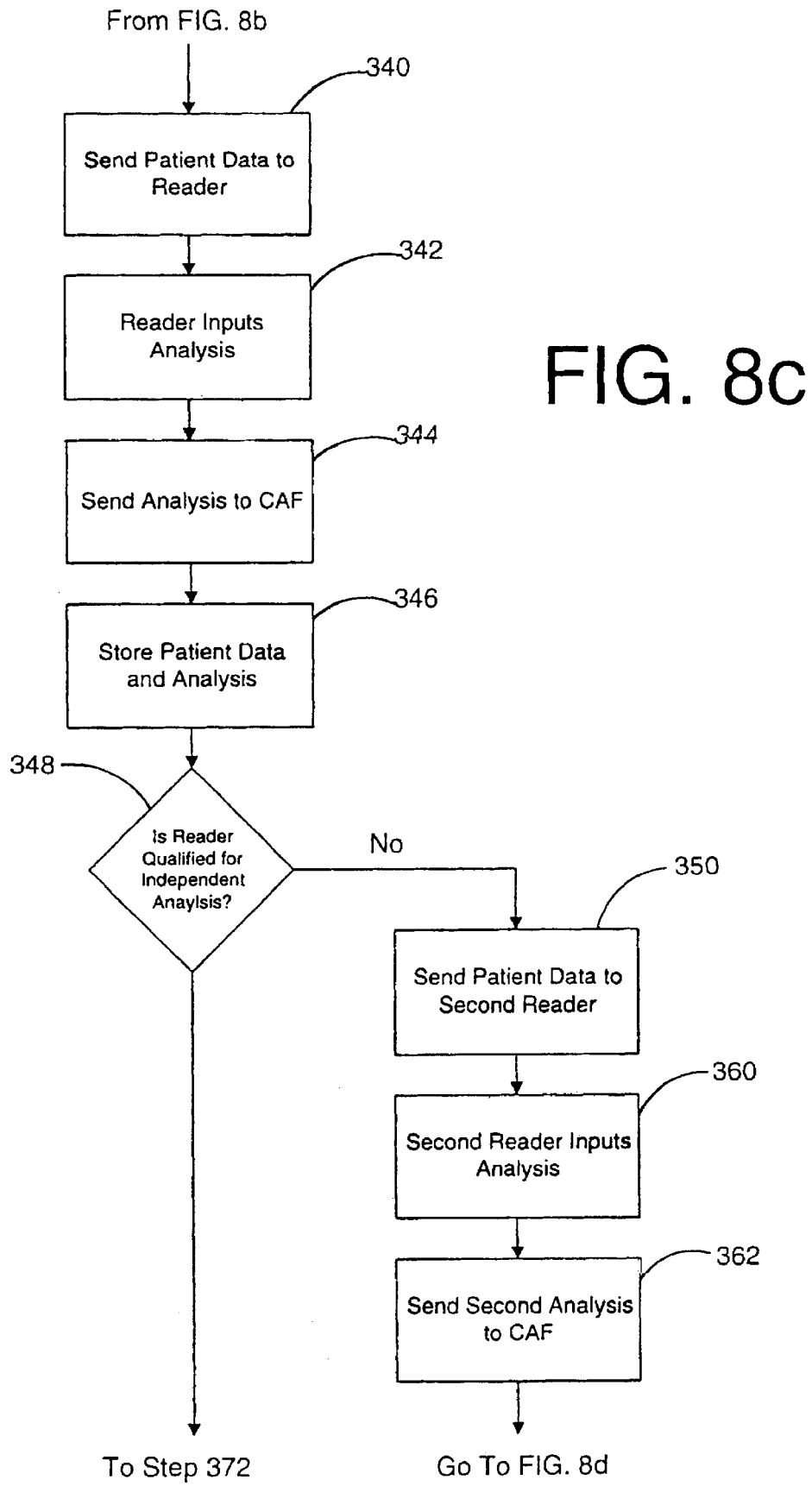

FIG. 8c illustrates the steps for reading images according to the present invention. After reviewing the patient eye image, the reader inputs their analysis in step 342. In a preferred aspect of the invention, the images and the patient data are embedded into or associated with a standardized data entry form having a variety of inputs matching generally recognized abnormalities appropriate for screening. In a preferred aspect, the reader need only check or "X" boxes representing their analysis of the patient's image to input their analysis.

Once the reader has input the analysis, the information is sent to the central analysis facility in step 344. As previously described, the analysis and patient image are relationally associated and will hereinafter be described as patient data. In a preferred aspect, either the individual reader or a reading center having multiple readers would retain the patient data, including the images, patient information and reader analysis, in data storage and a download would be conducted on a periodic basis to provide information to the central analysis facility. The information is stored at the central analysis facility in step 346. It will be appreciated that this information may be used both to provide the patient/requestor of the screening with feedback on the results of the screening as well as providing an indication of reading center and reader effectiveness.

In step 348, database information is accessed and analyzed concerning the qualification of the reader selected in step 320. Further, reader outputs may be sent for a second opinion on a periodic basis to assess quality regardless of the qualification of the reader. If the reader is qualified for independent analysis, then the method progresses to step 372 and the system determines whether the analysis reflects a risk factor associated with impaired vision or blindness. If it does not, notification of a favorable screening result is sent to the patient or requester in step 376. However, if a risk factor is detected, the patient information is sent to a follow-up database containing patient records needing further follow-up to recommend professional screening by optometrists or ophthalmologists. The patient information is also sent to the patient/requestor to inform them that it is appropriate for them to seek trained medical attention. In a preferred aspect of the present invention, each reader develops a diagnosis of the eye abnormality based on the patient eye image. However, the diagnosis is preferably used internally to assess reader quality and the patient is informed only of a positive screening for eye abnormalities without a specific diagnosis.

Returning to step 348, if the initial reader is not qualified for independent analysis, then the system progresses to step 350 where the patient data is sent to a second reader for a second opinion of the analyzed image. In a preferred aspect, the analysis of the first reader is not included with the patient data so that the second reader will not be influenced by the earlier analysis. In a preferred aspect of the invention, the second reader, typically of higher qualifications than the first reader, will not even be aware that the image has been previously reviewed by an earlier reader. In step 360, the second reader inputs their analysis and in step 362 the second reader sends the second analysis to the central analysis facility.

Figure 8D:
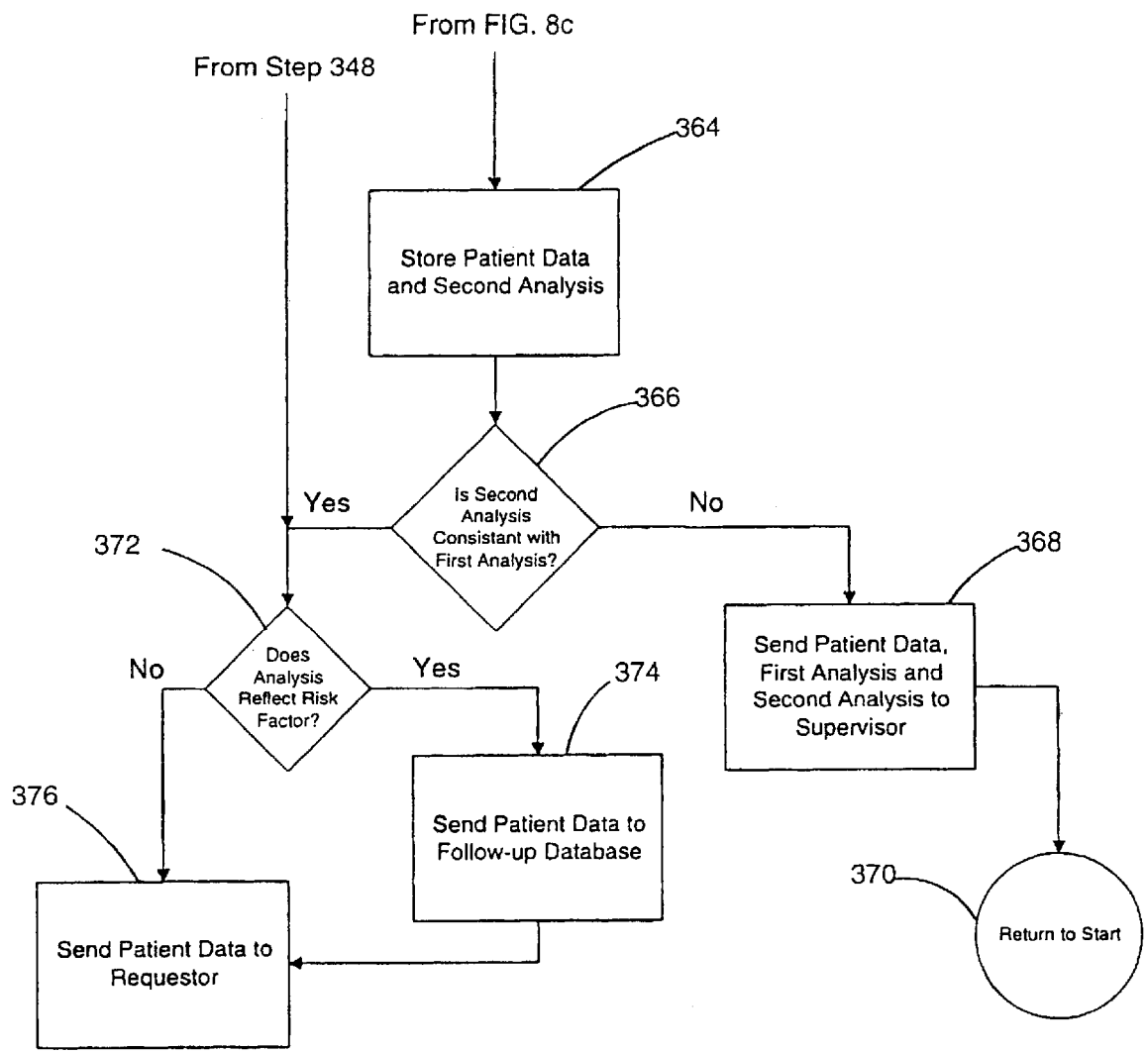

Referring to FIG. 8d, the methodology progresses with this information being stored as shown in step 364. In step 366, a comparison is made between the analysis of the first reader and the analysis of the second reader. If the analyses do not agree, the patient data including both first and second analysis are sent to a supervisor for resolution of the appropriate screening analysis of the patient eye image. Once the appropriate resolution has been reached, the screening methodology may proceed to step 372. The determination of the appropriate reading may be made by a single skilled supervisor in those cases where clear error has occurred. However, in difficult situations where discrepancies may not be easily resolved, it is preferred that a board of trained medical professionals review problematic images to assess the screening results and determine if professional review of the patient is warranted. If the comparison in step 366 reveals that the first and second analyses are consistent, the system progresses to step 372 and inquires whether a risk factor is present. If so, the follow-up database is updated with the information in 372 and the patient/requestor is provided with the information in step 376. If the comparison in step 366 reveals that the first and second analyses are not consistent, the result from the reader with higher rank is accepted as the official result. If the comparison in step 366 is not consistent and the readers have equal rank, the image is sent to the supervisor who's analysis is accepted as the official result.

Referring now to FIG. 9, a method for evaluating the quality of analysis is illustrated. More specifically, the present system contemplates a statistical evaluation of an individual reader or reading center to consider whether error rates are within satisfactory parameters. Referring now to FIG. 9, the system has started in step 410. This initial step may include accessing a database containing averages for populations with various abnormalities effecting vision. If statistically relevant, these abnormalities may be categorized across ethnic and racial backgrounds or socioeconomic status. Further, in the initializing start step of 410, patient data records for the reader and/or reading center are also accessed from the central analysis facility database. In a preferred aspect, a microprocessor analyzes the reader/reading center data in step 420 to assess whether enough analyses have been conducted to make statistical comparisons effective. If sufficient readings have not been conducted, then the system returns to start step 410. If sufficient readings have been conducted, the system progresses to step 430 where the results from the reader or reading center are compared to population statistics. The system progresses to step 440 which determines whether there is a deviation of the reading center results from the ranges of results expected from the population at large. The range of acceptable deviations may be adjusted depending on screening program parameters. If acceptable deviations do exist, the system further analyzes the data to specifically identify the areas of deviation in step 450. If there is no deviation, the program comes to an end in step 470.

The areas of deviation identified. in step 450 may include any of a variety of abnormalities arid may provide an indication of where additional training may be necessary to provide a higher selectivity for a reader or reading center for a particular abnormality. Thus, the system analyzes the deviations identified in step 450 and recommends in step 460 corrective action in that specific area of deviation. As previously mentioned, this can include additional training, multi-level review processes to assure accurate reading or other corrective measures to enhance the selectivity of the screening process. The system then comes to an end at step 470.

Figure 10A:
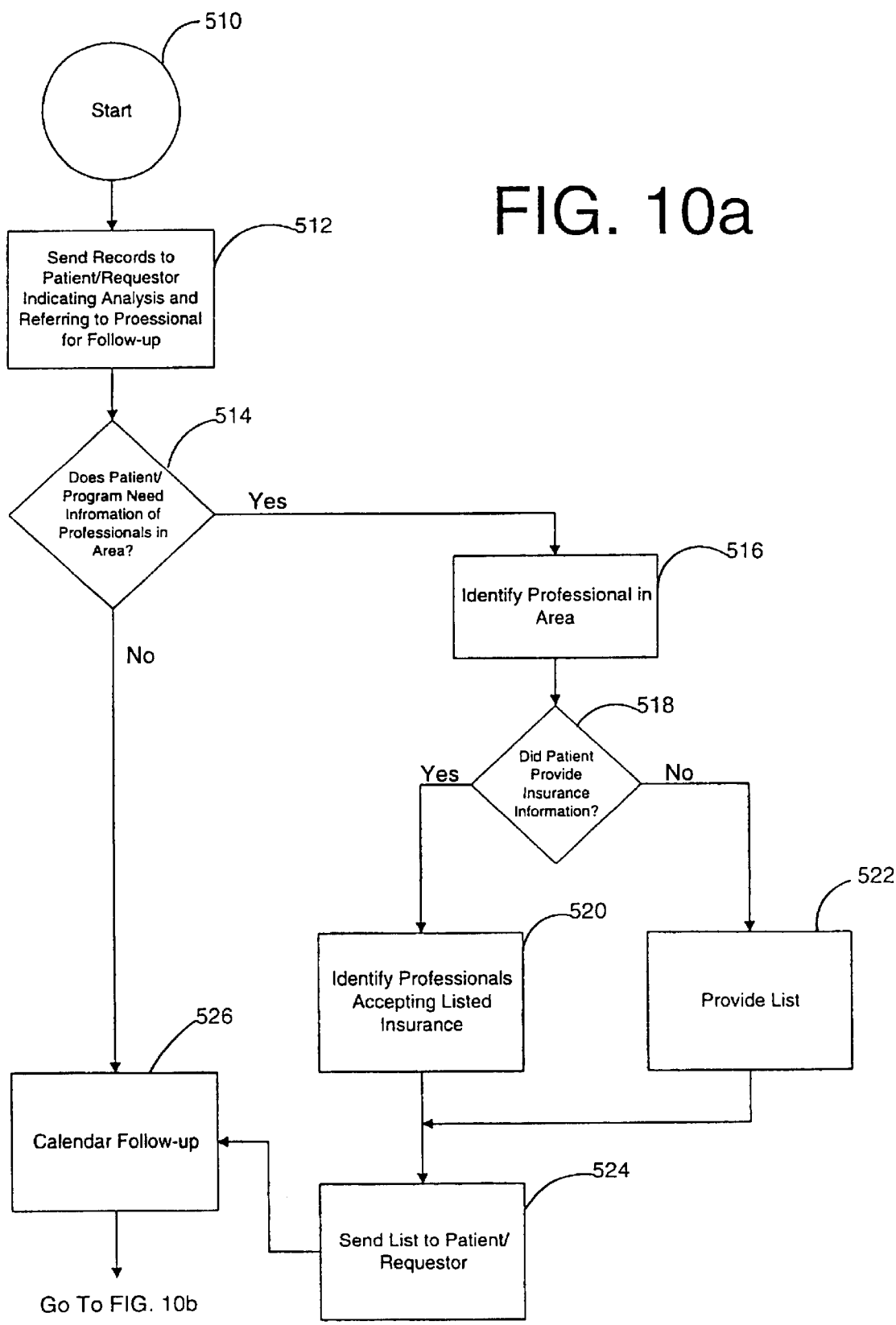

An important aspect to any screening program is an ability to assist people identified with various risk factors on following-up to receive the appropriate medical attention. With reference to FIGS. 10*a*–10*b*, a method is provided in accordance with the present invention to assist the at risk patient in obtaining the appropriate medical attention. The method starts in step 510 in which patient information is retrieved from the follow-up database and any external communications that may be necessary are established. In step 512, the central analysis facility sends records to patients and/or requesters indicating that the analysis has determined a positive risk factor for a vision problem and recommends a referral to a medical professional for a clinical follow-up visit. It is contemplated that in a preferred aspect, the system may automatically phone the patient or generate an e-mail. Further, the patient may be contacted by mail or any combination of direct and/or indirect contact. Further, in step 514, the system determines whether the patient or the screen program coordinator needs information about medical professionals within reasonable driving distance of the patient. If not, the system simply calendars a follow-up in step 526 for a further contact with the patient.

If the patient or program needs information about eye care professionals in their area, the system goes to step 516 where a database is consulted for a list of professionals within a particular area. As will be appreciated, area codes or mailing zip codes may be an effective means of determining physical proximity of the patient and medical professional. In step 518, the system further inquires whether the patient provided information concerning their insurance carrier. If they did, the system moves from step 520 to identified professionals selected in step 516 who also accept the patient's insurance. While not shown in the flow chart of FIG. 10*a*, if in step 520, there are no professionals from step 516 who accept the patient's insurance carrier, the patient may be provided with a list of professionals 516 and an indication that there is not information indicating that these professionals accept payment from their insurance carrier and the patient would be instructed to contact their insurance carrier with any questions. Once a list has been generated, in step 524, these lists of medical eye care professionals are sent to the patient and/or requesting institution. The system then moves to step 526 and calendars a follow-up date to again contact the patient.

The system then waits in step 528 for information from an eye care professional concerning the follow-up clinical evaluation of the patient. If no information has been received, it then looks to step 544 to determine whether it is time for a follow-up with the patient. If the answer to this inquiry in step 544 is negative, the system returns to step 528 in which it inquires whether information has been received from an eye care professional. If the answer in step 544 is positive, the central analysis facility again contacts the patient or notifies personnel of the need for further follow-up. Preferably, this continues until the patient has been contacted at least three times.

If information has been received from an eye care professional, the information is stored in the central analysis facility in step 530. For the purpose of quality assurance, in step 532, the eye care professional's diagnosis is compared to the readers analysis of the image. Preferably, in step 512, the patient receives a standardized form for the health care professional to complete and return, via fax, e-mail or mail, to the central analysis facility. If the analysis and diagnosis are the same, in step 542 the system updates the patient's records in the central analysis facility database indicating a positive match between the analysis and diagnosis. In step 536, if the comparison indicates a difference between the professional diagnosis and the readers analysis, the patient records are again retrieved and updated. However, the system continues on in step 534 and updates information for statistical review and error records and recommends in step 540 running a quality control analysis to evaluate the need for further action.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method for mass screening of patient's for ocular disease and abnormalities at locations remote from skilled analyzers trained to interpret eye images, comprising:

providing a remote site with a photoscreening device for generating a corneal reflection from a patient's eye and a device for recording images;

acquiring an image of at least one of the patient's eyes including the corneal reflection;

transmitting digital information corresponding to the acquired image to a central data facility;

selecting an image analyzer for evaluating the image of the patient's eye;

transmitting digital information to the image analyzer corresponding to at least one digital image of the patient's eye;

generating a diagnosis based on the digital image of the patient's eye;

sending the diagnosis to the central data facility; and providing the patient with recommendation generated by the image analyzer.

2. The method of claim 1, wherein said photoscreening device further includes a digital data storage capacity associated therewith.

3. The method of claim 2, wherein said photoscreening device includes a data entry component for receiving patient information.

4. The method of claim 2, wherein said transmitting further includes providing patient data gathered at the remote site in conjunction with the digital information corresponding to the acquired image.

5. The method of claim 2, further including storing the digital information corresponding to the acquired image in the data storage.

6. The method of claim 5, further including storing the digital information for multiple patients.

7. The method of claim 6, wherein said multiple patients is at least 5.

8. The method of claim 7, wherein said multiple patients is at least 10.

9. The method of claim 8, wherein said multiple patients is greater than 20.

10. The method of claim 6, further including waiting for a predetermined time before said transmitting.

11. The method of claim 10, wherein said time occurs once per day and multiple patient's information is submitted during said transmitting.

12. The method of claim 2, further including after said acquiring, creating a temporary digital connection between the data storage and the central data facility.

13. The method of claim 1, wherein the photoscreening device further includes a video display and after said acquiring the image is displayed on the video display and further including evaluating the image to determine if suitable for the analyzing.

14. The method of claim 1, further including storing test images in the central data facility having known diagnosis and transmitting test images to the image analyzer.

15. The method of claim 14, wherein said transmitting is done periodically.

16. The method of claim 1, further including sending digital information to a second image analyzer, generating a second diagnosis, sending the second diagnosis to the central data facility and comparing the first diagnosis to the second diagnosis.

17. A system for eye screening, comprising:
 a remote data entry device for receiving patient information;
 an eye imaging device for creating an image of at least one cornea of the patient;
 a transmitting device for electronically sending patient information and said image;
 a central data facility for receiving said patient information and said image; and
 a plurality of remote readers electronically connected to said central facility, wherein said central data facility sends said image to said readers for analysis and said readers return the analysis to the central data facility.

18. The system of claim 17, wherein said eye imaging device creates a digital image of at least one eye.

19. The system of claim 17, further including a plurality of remote data entry devices and eye imaging devices.

20. A method for reliable eye screening to detect abnormalities and diseases of the eye, comprising:
 sending electronic images of eyes to a reader for review;
 receiving reader analysis;
 creating one or more test images having pre-selected evidence of abnormality or disease; and
 periodically sending a test image to the reader to evaluate reliability of reader.

21. The method of claim 20, wherein the period between test images is adjusted based on prior reader performance.

22. The method of claim 20, wherein the test image is selected to test for a selected ocular abnormality or disease.

23. The method of claim 20, wherein the period and type of test image transmitted is based on comparing reader analysis to anticipated patient abnormalities.

* * * * *

UNITED STATES PATENT AND TRADEMARK OFFICE
CERTIFICATE OF CORRECTION

PATENT NO.   : 6,523,954 B1                                      Page 1 of 1
DATED         : February 25, 2003
INVENTOR(S)  : Ross A. Kennedy It is certified that error appears in the above-identified patent and that said Letters Patent is hereby corrected as shown below:

<u>Column 14,</u>
Line 24, please change "patient's" to -- patients --.

Signed and Sealed this

Fifteenth Day of July, 2003

JAMES E. ROGAN
*Director of the United States Patent and Trademark Office*